United States Patent [19]

Helzel

[11] Patent Number: 4,861,336
[45] Date of Patent: Aug. 29, 1989

[54] PUNCTURE CATHETER

[76] Inventor: Manfred W. Helzel, Frankenstrasse 29, 8700 Wurzburg, Fed. Rep. of Germany

[21] Appl. No.: 177,293

[22] Filed: Apr. 1, 1988

[30] Foreign Application Priority Data

Apr. 1, 1987 [DE] Fed. Rep. of Germany ....... 3710913

[51] Int. Cl.⁴ ..................... A61M 5/00; A61M 25/00
[52] U.S. Cl. ........................................ 604/95; 604/8; 604/53; 604/164
[58] Field of Search ................................. 604/51-53, 604/95, 158-169, 280-284, 8-10; 128/334 R, 343, 344, 348.1

[56] References Cited

U.S. PATENT DOCUMENTS 2,574,840  11/1951  Pieri et al. ............................. 604/95
4,222,380   9/1980  Terayama ......................... 604/164 X
4,668,226   5/1987  Omata et al. .................... 604/164 X Primary Examiner—Dalton L. Truluck
Attorney, Agent, or Firm—Fidelman & Wolffe

[57] ABSTRACT

A puncture catheter for transjugular or transfemoral percutaneous introduction into the lower vena cava is described. The catheter is composed of an outer direction catheter (1) and an inner puncturing catheter (5) introduced into it. The end segment (2) of the direction catheter (1) may be bent at an angle by means of a pulling mechanism (4), and directed toward the wall of the vena cava (V1). The tip of the puncture catheter (5) serves to perforate the wall of the vena cava (V1) and to puncture the portal vein (VP) ventrally crossing the vena cava (VCI). This non-anatomical connection is stabilized by accessory parts, a so-called porto-caval shunt.

10 Claims, 2 Drawing Sheets

PUNCTURE CATHETER

SUMMARY OF THE INVENTION

The invention concerns a puncture catheter to establish a porto-caval shunt from the lower vena cava, which is introduced transjugularly or transfemorally percutaneously into the vena cava.

The porto-caval shunt, i.e., the non-anatomical connection, in patients suffering from liver disease, is currently established in a relatively major operation. This is frequently an emergency operation with high mortality. The cause is usually excess pressure arising in the portal circulation.

The task of the invention is to create an intravascular puncture catheter of the type mentioned at the start, with which a non-anatomical connection can be established between the portal vein on the one hand and the lower vena cava on the other hand, to equilibrate high pressure in the portal circulation.

This task is accomplished by a puncture catheter of the kind mentioned at the start, in that an external directing catheter is provided, flexible at least at its inserted end segment, and presenting at this end segment a pulling mechanism, operated from outside, to bend the end segment at an angle and guide it; and in that an internal puncture catheter with an open catheter tip can be inserted into the directing catheter, and serves to perforate the wall of the vena cava and to puncture the portal vein ventrally crossing the vena cava.

Useful further developments are characterized in the subclaims.

With such a puncture catheter, a porto-caval shunt can be established in cases of liver disease accompanied by portal hypertension, so as to equillibrate high pressure in the portal circulation. The tip of the two-part catheter is so designed that it is possible to puncture the portal vein from the lumen of the lower vena cava, using a catheter introduced transjugularly or transfemorally percutaneously. The design of the catheter tip of the puncture catheter as a cannula whose lumen communicates with the lumen of the puncture catheter, allows blood to be aspired so as to monitor the successful puncture of the portal vein. Accessory parts for the puncture catheter can be used to improve its functioning.

The invention is explained in more detail from examples shown purely schematically in the drawings.

DESCRIPTION OF THE PREFERRED EMBODIMENTS

The puncture catheter consists essentially of two parts: A directing catheter 1 and the actual puncture catheter 5, guided along the directing catheter 1, both Fthe side and pointed toward the wall of the vena cava V1.

Into this directing catheter 1, the internal puncture catheter 5 is inserted, making it possible to perforate the wall V1 of the vena cava and the portal vein VP which ventrally crosses the vena cannula 7, whose lumen communicates with the lumen of the puncture catheter 5.

Figure 1:
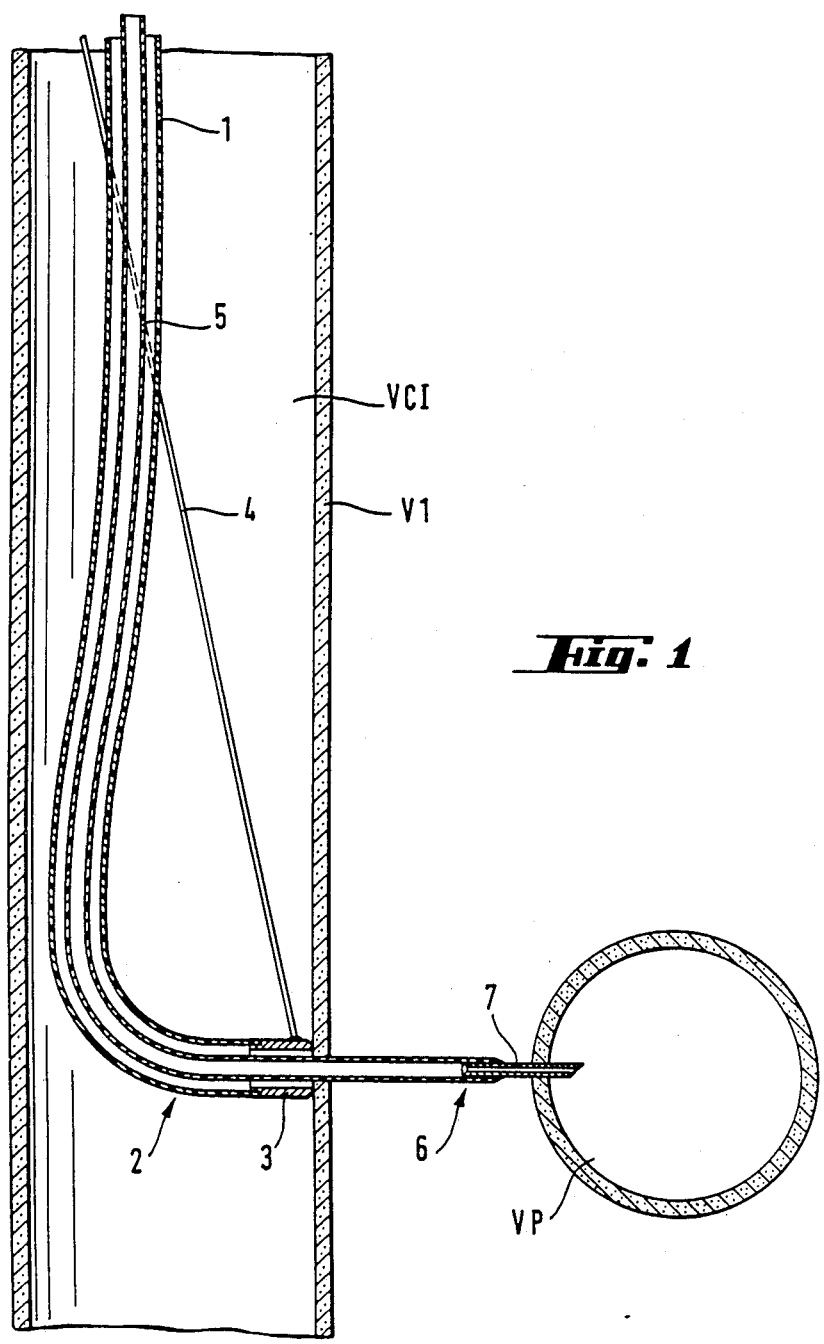
FIG. 1 shows a schematic side view of a two-part catheter introduced into the vena cava.

The portal vein VP is shown in FIG. 1 in cross section, and thus in its position relative to the vena cava. The tip 6 of the puncture catheter 5 is guided to the wall of the portal vein VP.

Figure 2:
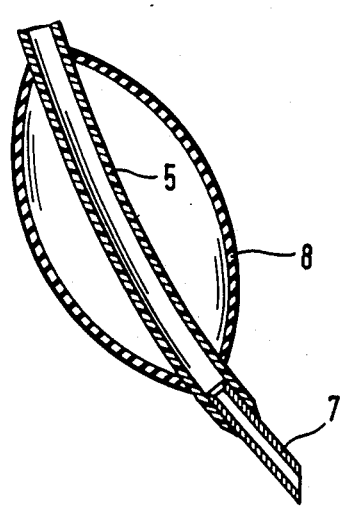
FIGS. 2, 3 and 4 show various additional parts for the puncture catheter.
Figure 3:
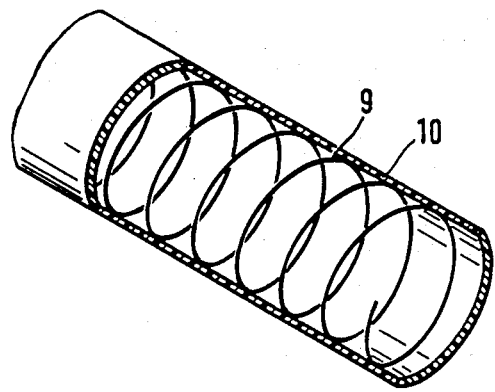
Figure 4:
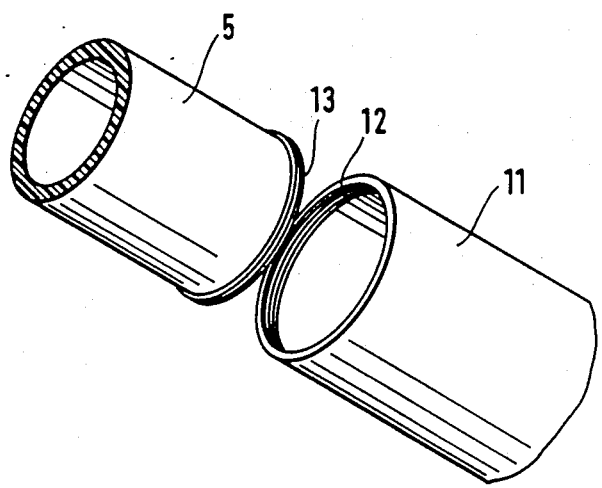

Accessory parts to the puncture catheter 5 are shown schematically in FIGS. 2 to 4. These essentially serve to expand and stabilize the non-anatomical connection, produced by puncture, between the respective lumens of the lower vena cava VCI and of the portal vein VP.

FIG. 2 shows a metal-coated, inflatable balloon 8, applied directly to the puncture catheter 5. But it may also be configured as an additional, separate part, and used with the puncture catheter 5. The electrical conductivity of the surface of this balloon 8 allows an expansion and electrical scabbing of the walls of the porto-caval shunt.

FIG. 3 shows a metal spiral 9, surrounded by a thin membrane 10 or alternatively provided on its inner walls with a plastic coating to prevent thrombosis.

FIG. 4 shows a plastic cylinder 11, which may if applicable be inflated, and which is removably attached to the catheter tip. This attachment may for example be accomplished via a screw connection, in which an internal threading in the hollow cylinder 11 is screwed together with an external threading 13 on the catheter tip.

I claim:

1. A catheter suitable for establishing a porto-caval shunt, comprising:
    a directing catheter having an inserted end segment, said directing catheter being flexible at least at the end segment;
    a pulling mechanism located outside said directing catheter and attached to an outer surface of said end segment so as to selectively bend and guide the end segment; and
    a puncutre catheter located inside said directing catheter and having an open catheter tip which can extend past the end segment of said directing catheter.

2. The catheter as claimed in claim 1, wherein the end segment of the directing catheter has a tip which is made of metal.

3. The catheter as claimed in claim 1, wherein said puncture catheter comprises a lumen, and said catheter tip comprises a cannula having a lumen which communicates with the lumen of the puncture catheter.

4. The catheter as claimed in claim 1, further comprising a metal-coated inflatable balloon fixed to the puncture catheter.

5. The catheter as claimed in claim 1, further comprising a metal-coated inflatable balloon removably attached to the puncture catheter.

6. The catheter as claimed in claim 1, wherein said puncture catheter comprises a metal spiral coated with a thin membrane.

7. The catheter as claimed in claim 6, wherein said thin membrane is located inside said metal spiral and is made of plastic.

8. The catheter as claimed in claim 1, further comprising a hollow cylinder removably attachable to the catheter tip of said puncture catheter.

9. The catheter as claimed in claim 8, wherein said hollow cylinder is inflatable.

10. A method for establishing a porto-caval shunt between the vena cava and the portal vein ventrally crossing the vena cava, comprising:
    introducing a directing catheter transjugularly or transfemorally percutaneously into the lower vena cava, said directing catheter having an inserted end segment and being flexible at least at the end segment;

guiding and bending the end segment of the directing catheter, using a pulling mechanism located outside said directing catheter and attached to an outer surface of said end segment, so as to position said end segment at a desired position in the vena cava;

inserting a puncture catheter having an open catheter tip into the directing catheter so that said open catheter tip extends past the end segment of said directing catheter and perforates the wall of the vena cava;

inserting said puncture catheter further into the directing catheter so as to puncture the portal vein ventrally crossing the vena cava.

* * * * *

UNITED STATES PATENT AND TRADEMARK OFFICE
CERTIFICATE OF CORRECTION

PATENT NO. : 4,861,336

DATED : August 29, 1989

INVENTOR(S) : Manfred W. Helzel

It is certified that error appears in the above-identified patent and that said Letters Patent is hereby corrected as shown below:

At column 1, in between lines 61 and 62, add:

--of these being inserted into the vena cava VCI.

The directing catheter 1 is flexible, at least in its end segment 2 that is inserted, and presents a hard tip 3, preferably of metal. A pulling mechanism 4 is attached to the flexible end end segment 2. With this pulling mechanism 4, operated from outstide, the end segment 2 of the directing catheter 1 can be bent off to--

At column 1, line 62, delete "F" at the beginning of the word "the".

UNITED STATES PATENT AND TRADEMARK OFFICE
CERTIFICATE OF CORRECTION

PATENT NO. : 4,861,336

DATED : August 29, 1989

INVENTOR(S) : Manfred W. Helzel

It is certified that error appears in the above-identified patent and that said Letters Patent is hereby corrected as shown below:

In claim 1, at column 2, line 36, correct the spelling of the word "puncture".

Signed and Sealed this

Fourteenth Day of August, 1990

Attest:

HARRY F. MANBECK, JR.

*Attesting Officer*     *Commissioner of Patents and Trademarks*